United States Patent [19]

Farrelly et al.

[11] Patent Number: 4,898,180
[45] Date of Patent: Feb. 6, 1990

[54] PERSONAL BLOOD PRESSURE MONITOR

[76] Inventors: Susan E. Farrelly, 150 East 69th St., New York, N.Y. 10021; George Spector, 233 Broadway, Rm. 3815, New York, N.Y. 10007

[21] Appl. No.: 100,299

[22] Filed: Sep. 23, 1987

[51] Int. Cl.$^4$ .............................................. A61B 5/02
[52] U.S. Cl. ..................................... 128/681; 128/683; 128/689
[58] Field of Search ............... 128/672, 677, 680–683, 128/687–688, 689–690, 684–686, 688, 670–671

[56] References Cited

U.S. PATENT DOCUMENTS

| | | | |
|---|---|---|---|
| 4,185,621 | 1/1980 | Morrow | 128/690 X |
| 4,252,127 | 2/1981 | Gemelke | 128/683 X |
| 4,407,295 | 10/1983 | Stever et al. | 128/670 |
| 4,469,107 | 9/1984 | Asmar et al. | 128/681 |
| 4,493,326 | 1/1985 | Hill et al. | 128/680 |

FOREIGN PATENT DOCUMENTS

| | | | |
|---|---|---|---|
| 0653845 | 1/1986 | Switzerland | 128/672 |
| 2087238 | 5/1982 | United Kingdom | 128/680 |

OTHER PUBLICATIONS

Wegmann et al.; WO86/06603, 11-1986.

*Primary Examiner*—Angela D. Sykes

[57] ABSTRACT

A blood pressure monitoring device is provided and consists of a cuff to be worn on the arm and a digital watch to be worn on the wrist that will allow an individual to monitor their blood pressure over a given period of time while engaging in normal daily activities. The device will sound an alarm if the blood pressure readings are above or below normal readings programmed with the device and can be programmed to record readings taken at preset time intervals and display such readings when desired.

4 Claims, 1 Drawing Sheet

PERSONAL BLOOD PRESSURE MONITOR

BACKGROUND OF THE INVENTION

The instant invention relates generally to measuring devices and more specifically it relates to a blood pressure monitoring device.

Numerous measuring devices have been provided in prior art that are adapted to indicate the blood pressure of people. For example, U.S. Pat Nos. 3,189,024; 3,557,779 and 3,754,545 all are illustrative of such prior art. While these units may be suitable for the particular purpose to which they address, they would not be as suitable for the purposes of the present invention as heretofore described.

SUMMARY OF THE INVENTION

A primary object of the present invention is to provide a blood pressure monitoring device that will overcome the shortcomings of the prior art devices.

Another object is to provide a blood pressure monitoring device that will allow an individual to monitor thie blood pressure over a given period of time while engaging in their normal daily activities.

An additional object is to provide a blood pressure monitoring device that would sound an alarm if at any time the blood pressure readings are above or below those programmed allowing the wearer to monitor serious fluctuations in the readings.

Another object is to provide a record of blood pressure readings at programmed intervals over a specific period of time which are stored in memory bank for recall on the display screen when desired.

A further object is to provide a blood pressure monitoring device that is simple and easy to use.

A still further object is to provide a blood pressure monitoring device that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

DETAILED DESCRIPTION OF THE PREFERRED EMBODIMENTS

Figure 1:
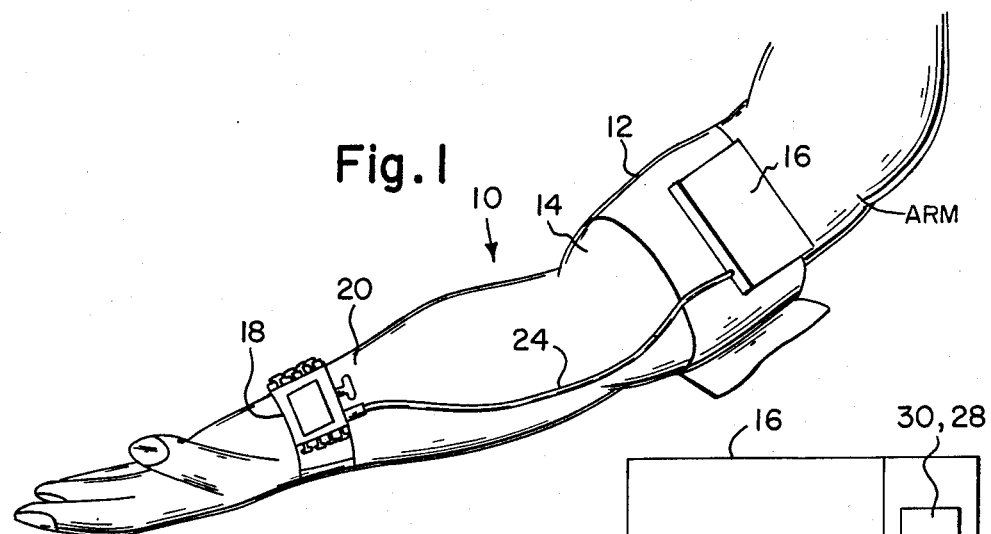
FIG. 1 is a perspective view of the invention on an arm and wrist of a person.
Figure 2:
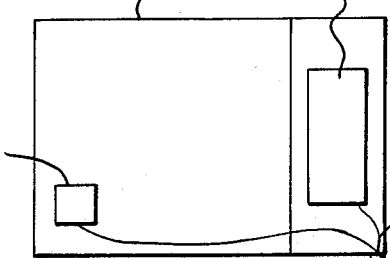
FIG. 2 is a diagrammatic view of the housing for the cuff with pump, solenoid and microphone shown therein.
Figure 3:
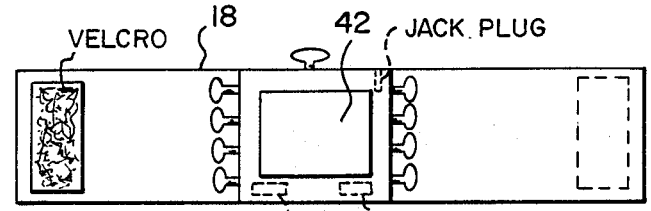
FIG. 3 is a top flat plan view of the watch.
Figure 4:
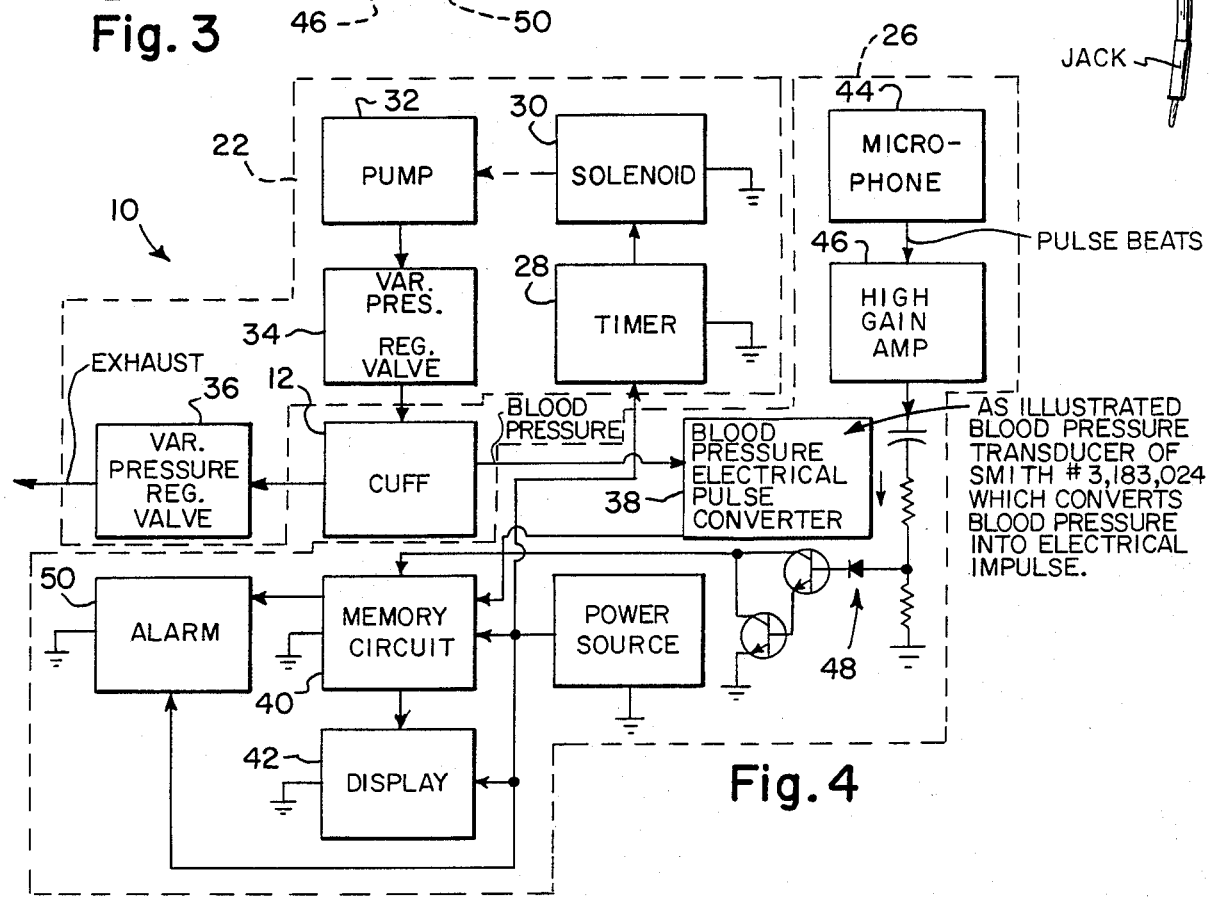
FIG. 4 is a block and electrical diagram view of the electrical and mechanical systems of the invention down in combination thereof.

Turning now descriptively to the drawings, in which similar reference characters denote similar elements throughout the several views, FIGS. 1 through 4 illustrate a blood pressure monitoring device 10 consisting of a cuff 12 adapted to encircle an arm 14 of a person, a housing 16 on the cuff 12 and a digital watch 18 is adapted to encircle a wrist 20 of the person. A pressure regulating unit 22 extends from the digital watch 18 to the housing 16 via cord 24 for inflating the cuff 12. The pressure regulating unit 22 is controlled from the digital watch 18 to inflate the cuff 12 at predetermined time intervals. A monitoring unit 26 extends from the cuff 12 and the housing 16 to the digital watch 18. The monitoring unit 26 is responsive to intensity of blood pressure pulses from the person coming through the housing 16 into the digital watch 18.

The pressure regulating unit 22 includes a timer 28 located within the digital watch 18. A solenoid 30 within the housing 16 is connected to the timer 28. A pump 32 within the housing 16 is connected to the solenoid 30 in which the pump 32 supplies a source of fluid, such as air, under pressure to the cuff 12 by activation of the solenoid 30 by the timer 28. A first variable pressure regulator valve 34 is adapted to be connected between the pump 32 and the cuff 12 and is responsive to a first preselected pressure of the cuff 12 shutting off the flow of fluid from the pump 32 to the cuff 12. A second variable pressure regulator valve 36 is responsive to a second preselected pressure in the cuff 12 for exhausting the pressurized fluid in the cuff to deflate the cuff.

The monitoring unit 26 includes a blood pressure to electrical impulse converter 38 located within the cuff 12. The converter 38, as illustrated functions as the blood pressure transducer of Smith U.S. Pat. No. 3,189,024 which translates blood pressure into variable electrical impulses. A memory circuit 40 located within the digital watch 18 is connected to the converter 38 via cord 24 for receiving the electrical impulses therefrom. A display 42 located on the digital watch 18 is connected to the memory circuit 40 for displaying the blood pressure pulse readout.

The monitoring unit 26 further includes a transducer 44, such as a microphone, within the housing 16 for converting heart beat pulses into electrical signals. A relatively high gain amplifier 46 is located within the digital watch and is connected to the transducer 44 for producing an output signal therefrom. A circuit 48 as illustrated functions as the electrical circuitry shown in FIG. 4 in blood pressure recording device of Weinstein U.S. Pat. No. 3,557,779. The circuit 48 amplifies the output signal from amplifier 46 into a greater current signal to be received by the memory circuit 40. An alarm 50 located within the digital watch 18 will receive the greater current signal from the memory circuit 40 when readings of the heart beat pulses are above and below normal readings programmed within the memory circuit 40.

The memory bank circuit can be provided with a timer or other conventional equipment which will record and store blood pressure readings at pre set time intervals which can then be recalled for viewing on display 42 when desired.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A blood pressure monitoring device which comprises:

(a) a cuff inflatable to a desired pressure adapted to encircle an arm of a person;
(b) a housing on said cuff;
(c) a digital watch adapted to encircle the wrist of the person provided with means for controlling said pressure and for displaying pulse and blood pressure readings;
(d) a pressure regulating means extending from said digital watch to said housing for inflating said cuff, said pressure regulating means controlled from said digital watch by the first said means to inflate said cuff at predetermined time settings;
(e) a monitoring unit extending from said cuff and said housing to said digital watch, said monitoring unit being responsive to intensity of blood pressure pulses from the person coming through said cuff and heart beat pulses from the person coming through said housing into said digital watch; and
(f) means for recording blood pressure readings at preset time intervals wherein said readings can be displayed on said watch.

2. A blood pressure monitoring device as recited in claim 1, wherein the first said means includes a timer responsive to preset time settings on the watch and wherein said pressure regulating means includes:
(a) a solenoid within said housing activated by said timer at said time settings;
(b) a pump within said housing connected to said solenoid, said pump supplying a source of fluid under pressure to said cuff by activation of said solenoid;
(c) a first valve means connected between said pump and said cuff and being responsive to a first preselected pressure of said cuff for shutting off the flow of fluid from said pump to said cuff;
(d) a second valve means responsive to a second preselected pressure in said cuff for exhausting the pressurized fluid in said cuff to deflate said cuff.

3. A blood pressure monitoring device as recited in claim 2, wherein said monitoring unit includes:
(a) a blood pressure to electrical impulse converter located within said cuff;
(b) a memory circuit means located within said digital watch connected to said converter for receiving the electrical impulses therefrom for storage and recall display; and
(c) a display means located on said digital watch connected to said memory circuit means for displaying the blood pressure pulse readout either of a preset reading or of a reading that has been stored in the memory circuit means.

4. A blood pressure monitoring device as recited in claim 3, wherein said monitoring unit further includes:
(a) a transducer within said housing for converting heart pulses into electrical signals;
(b) a relatively high gain amplifier means located within said digital watch connected to said transducer for producing an output signal therefrom;
(c) means for amplifying the output signal into a greater current signal to be received by said memory circuit means; and
(d) an alarm means located within said digital watch for receiving the greater current signal from the memory circuit means when readings of the heart beat pulses are above and below normal readings programmed within said memory circuit means.

* * * * *